United States Patent [19]

Cŏupek et al.

[11] 3,983,001

[45] Sept. 28, 1976

[54] ISOLATION OF BIOLOGICALLY ACTIVE COMPOUNDS BY AFFINITY CHROMATOGRAPHY

[75] Inventors: Jiri Cŏupek, Prague; Jaroslava Truková, Cesky Brod; Olga Hubálková, Prague; Miroslava Kriváková, Prague; Viktor Mansfeld, Prague, all of Czechoslovakia

[73] Assignee: Ceskoslovenska akademie ved, Prague, Czechoslovakia

[22] Filed: Feb. 12, 1976

[21] Appl. No.: 657,601

Related U.S. Application Data

[63] Continuation-in-part of Ser. No. 357,814, May 7, 1973, abandoned.

[30] Foreign Application Priority Data

May 10, 1972 Czechoslovakia .................. 3136-72

[52] U.S. Cl. ................................ 195/66 R; 195/63; 195/DIG. 11; 260/112 R
[51] Int. Cl.² .......................................... C07G 7/02
[58] Field of Search ....... 195/66 R, 63, 68, DIG. 11; 260/112 R

[56] References Cited
UNITED STATES PATENTS

| 3,746,622 | 7/1973 | Nishikawa et al. ................. 195/66 R |
| 3,834,990 | 9/1974 | Werle et al. .......................... 195/68 |

OTHER PUBLICATIONS

Cuatrecasas et al., article in Methods in Enzymology, vol. 22, pp. 345–378, (1971).
Feinstein in Naturwissenschaften, vol. 58, No. 8, pp. 389–396, (1971).

Primary Examiner—Lionel M. Shapiro

[57] ABSTRACT

A method for the isolation of biologically active compounds by affinity chromatography comprising forming a sorption complex between a solvent soluble biologically active compound to be isolated and biologically active compound linked to a solid carrier by a covalent bond, said solid carrier being a hydrophillic macroporous copolymer.

23 Claims, No Drawings

ISOLATION OF BIOLOGICALLY ACTIVE COMPOUNDS BY AFFINITY CHROMATOGRAPHY

CROSS-REFERENCE TO RELATED PATENT APPLICATION

This application is a continuation-in-part of copending U.S. patent application Ser. No. 357,814, filed May 7, 1973 now abandoned, the disclosure of which is incorporated herein by reference.

This invention relates to a method of isolating biologically active compounds upon selective sorbents by affinity chromatography, that is, by selective adsorption. More particularly this invention relates to methods for isolating biologically active compounds such as enzymes, coenzymes, enzyme inhibitors, antibodies, antigens, hormones, carbohydrates, such as monosacharides, disacharides, polysacharides, and the like. The invention also relates to the selective adsorption of lipids such as triglycerides, fats, oils, waxes, phospholipids, glycolipids, and sterols, as well as carotenoids, amino acids, peptides, proteins, and the like as well as nucleotides nucleic acids, vitamins such as Vitamin B and the like.

Affinity chromatography can be further applied when it is desired to concentrate dilute solutions of proteins in order to remove denatured forms thereof from refined proteins, and in the separation and resolution of protein and peptide components which have originated in specific chemical modifications.

A number of materials have been used in the prior art as sorption complex carriers for biologically active components in affinity chromatography. Among those materials known in the art, there may be mentioned, copolymers of styrene and di-vinyl benzene; copolymers of acrylamide with alkylene bis-acrylamide; polysacharides; porous glass, etc. Many of the prior art materials have proved undesirable and possess many disadvantages due to the fact that they carry thereon linked inorganic functional groups and thereby, exhibit considerably non-specific and hence nondiscriminating sorption of the biologically active material. In other words, the prior art materials are neither selective nor specific enough to be of any great use. Other prior art materials possess unsuitable mechanical, hydrolytical, microbial, or thermal stabilities, as well as unstable distribution of pore sizes and, accordingly, have but a rather limited range of use. Homogeneous hydrophilic gels which are presently on the market, are only of use when they are moist and do not dry out. This latter requirement makes their storage and transport rather difficult and, hence, their use and availability for the above affinity chromatography quite unsatisfactory.

It is known in the prior art that the most accurate and sophisticated separation methods operable in the biochemical arts are the processes based on the ability of great numbers of biologically active compounds to form sorption complexes with other biologically active compounds. The character of this complex-formation or inter-attraction is ordinarily quite specific to the biologically active compound being selectively adsorbed and is, furthermore, reversible with regard thereto, i.e., the adsorbed component may be released. In practive, the process works as follows: A component of the sorption complex sought to be insolubilized is first linked to a solid carrier material by a covalent bond; that treated carrier is thereby brought in contact with a solution of a complex mixture of compounds, one of which is the biologically active compound sought to be adsorbed at suitable reaction conditions; only the compounds possessing a specific affinity for the biologically active linked component will be selectively adsorbed from the complex mixture onto the surface of the adsorption complex carrier.

A reversal of the above process, or a dissociation of the adsorption complex and separation of the soluble components thereof from the component adsorbed or linked to the biologically active carrier surface, or gel, as it may be called, occurs by varying the pH, the ionic strength of the solvent, the temperature thereof, and the like. The aforementioned process is of particular application in the separation and refining of enzymes, enzyme inhibitors, antibodies, antigens, nucleic acids, proteins linked to co-enzymes, and/or vitamins, repressor proteins, proteins with boundary scepters of toxins or hormones, proteins containing sulf-hydro groups, synthetically prepared peptides, and the like, including those biologically active components mentioned hereinabove.

It is an object of the instant invention to avoid one or more drawbacks of the prior art.

It is generally understood that the macroporous hydrophilic carrier (hydrogel) is a copolymer defined as a material with large inner surface of the pores measurable in the dry state and having physically stable pores, e.g., channells even in the contact with the solvent. This property gives the carriers a considerable mechanical strength and binding capacity in contrast to homogeneous xerogels mentioned in the prior art. This property makes the most important difference to all materials in the prior art.

It is another object of the invention to provide for a method for the isolation of biologically active compounds by affinity chromatography.

It is still another object of the instant invention to provide for a method of carrying out affinity chromatography upon selective adsorbents.

It is a further object of the instant invention to carry out the above process by forming an adsorption complex between the compound which is desired to be isolated and the biologically active compound linked to a solid carrier.

It is still another object of the instant invention to carry out the process by using as solid carrier, a hydrogel carrier.

These and other objects of the invention will become apparent as the description proceeds.

Broadly speaking, the instant invention relates to a method for the isolation of biologically active compounds by affinity chromatography by taking advantage of the formation of sorption complexes between a soluble compound (biologically active) which is desired to be isolated and a biologically active compound (which need not be the same compound) which is linked to a solid hydrogel carrier by a covalent bond therebetween.

The carriers contemplated by the instant invention are the hydrophilic macroporous copolymers of hydrophilic monomers, such as: hydroxyloweralkylacrylates, i.e., methyl, ethyl, propyl, and through octyl; hydroxyloweralkylmethacrylates; oligo- or polyglycol acrylates; oligo- or polyglycol methacrylates; acrylonitriles; methacrylonitriles; aminoloweralkylacrylates (aminoloweralkylmethacrylates); acrylic or methacrylic acid and methylolacrylamide, polymerized with a cross-linking agent, such as: di-vinyl or polyvinyl monomers, such as, alkylene di-acrylates; alkylene dimethacrylates, oligo- or polyglycoldiacrylates, oligo- and polyglycoldimethacrylates; alkyl triacrylates and trimethacrylates; glycoltriacrylates or trimethacrylates; alkyl polyacrylates or polymethacrylates; glycolpolyacrylates or polymethacrylates, alkylene-bis-acrylamides, alkylene-bis-methacrylamides, or di-vinyl benzenes. The hydrophilic gels referred to above are employed in carrying out the instant invention by virtue of their chemically linked biologically active compounds therein in a gel known as the first phase, which phase is brought into contact with a solution containing at least the compound which is desired to be separated therefrom. Components which are operative to form the sorption complex are then selectively sorbed and form a covalent link with the modified gel under given conditions in this first phase. In a second phase, the biologically active compounds which had been sorbed are desorbed and separated from the gel by changing the environment thereof, i.e., by changing the physical or physicochemical conditions, without, however, causing any damage to the activity of either the still linked if any, of the desorbed components. The cycle of the specific sorption and physico-chemical desorption may be repeated as long as the biological activity of the compound linked to the gel lasts.

The gel material is based essentially upon hydrophilic esters of acrylic and methacrylic acids and can advantageously be used in the form of their discrete particles, preferably globular particles, or in the form of blocks, membranes, films, fibers, tapes, moving belts, or in any physical form so long as the gel material is operative to provide a necessary area of contact with the mixture containing the biologically active material sought to be separated therefrom.

It is noted that acrylamide and methacrylamide are unsuitable as the primary monomer because the resultant polymer possess unsuitable mechanical, hydrolytic or thermal stability, as well as an inconsistant distribution of pore size and a lower molecular weight exclusion limit. Similar difficulties are encountered with methylene-bis-acrylamide or methacrylamide except that as cross-linking agents the alkylene-bis-acrylamides yield a lower hydrolytic stability but are otherwise acceptable. Cross-linking agents are always used in minor amounts in order to obtain insolubility or to control the swellng capacity and do not markedly affect the chemical properties of the resultant polymers.

Similarly, it is noted that di-vinyl benzene is acceptable as a cross-linking agent, but styrene-di-vinyl benzene is hydrophobic and possesses considerable non-specificity and hence results in the non-discriminatory sorption of biologically active materials and is unacceptable.

Preparation of the hydrogel copolymers useful as the carrier is carried out in accordance with polymerization procedures well known in the art as is the formation of the physical form thereof ultimately employed.

It is to be understood, that throughout the disclosure herein, the method is described either by using a biologically active compound bound in the gel, which compound corresponds to that sought to be separated, or by using a different biologically active compound. It is not necessary that both compounds be the same; however, the ability of one biologically active compound to separate either a like compound or a dissimilar one is dependent upon the following: The isolation makes use of the ability of biologically active substances to form specific reversible complexes with other active substances. E.g., enzymes form specific complexes with their inhibitors, antibodies with antigens, toxins with antitoxins, receptors with hormones, etc. If one component of the specific complex is bound to a solid carrier, it is possible to adsorb the other component from the solution.

The isolated biologically active compounds are prevented from denaturation by stabilizing their tertiary structure employing ligand links to the active centers thereof. The entire process is relatively rapid and enables one to obtain highly active products in only one operation. Considerable mechanical and hydrolytical stabilities of the hydrophilic macroporous carriers permit their use in the most convenient form for a given application in production.

The above separation technique may be carried out either discontinuously by a batch method or continuously in repeated cycles, such as in a column or the like. In the continuous process, the gel carrier may be moved as a continuous medium, such as a belt or tape, along a conveyor mechanism and the solutions to be acted upon are stationary with respect thereto or a container holding the solution may move in the opposite direction.

A great advantage of the separation by affinity chromatography performed in the above described manner is one rapid separation of the isolated biologically active compounds from inhibitors and destructive contaminants.

All methods suitable for carrying out affinity chromatography as are known in the art are incorporated herewith by reference.

The physical apparatus and/or technique employed in the actual separation method (i.e., discontinously or batch) is not critical to the invention and accordingly any of the well known procedures are operative.

The instant invention, broadly includes the provision of a method for the isolation of biologically active compounds by affinity chromatography comprising forming a sorption complex between a solvent soluble biologically active compound to be isolated and a biologically active compound linked to a solid carrier by a covalent bond, said solid carrier being a hydrophilic macroporous copolymer derived from hydrophilic monomers selected from the group consisting of hydroxyalkyl acrylates, hydroxyalkyl methacrylates; oligo- and polyglycol acrylates, oligo- and polyglycol methacrylates; acrylonitrile, methacrylonitrile; aminoalkyl acrylates, aminoalkyl methacrylates; acrylic acid, methacrylic acid or methylolacrylamide and cross-linked by copolymerization with divinyl or polyvinyl monomers selected from the group consisting of alkylene diacrylates, alkylene dimethacrylates, oligo- and polyglycol diacrylates, oligo- and polyglycol dimethacrylates, alkyl tri- and polyacrylates, alkyl tri- and polymethacrylates, glycol tri- and poly- acrylates, glycol tri- and polymethacrylates, alkylenebis acrylamides, alkylenebismethacrylamides and divinylbenzene.

In a broader aspect of the invention, it is seen that the copolymer can comprise a hydrophilic monomer selected from the group consisting of hydroxy alkyl acrylates and methacrylates, polyglycol acrylates and methacrylates, acrylonitrile and methacrylonitrile, aminoalkyl acrylates and methacrylates, acrylic and methacrylic acid or methylolacrylamide copolymerized with another member of said group as well as derivatives of acrylic and methacrylic acid such as substituted amides, alkyl esters and anhydrides or copolymerized with a minor amount of the above noted polyolefinic cross-linking agents.

Initially, the hydrogel-sorption complex is formed by first preparing a hydrogel (as above defined) in accordance with copolymerization condition and techniques well known in the art. The thus prepared hydrogel is thereafter brought into contact with a solution containing at least, in soluble form, the biologically active material sought to be later isolated. The biologically active component may be present in the solution in amounts of mg to kg, in dependence on its solubility and on the capacity of the gel. The solvent for the biologically active compound may be any one of the following aqueous electrolytes and organic water- miscible solvents. The hydrogel is brought into contact with the liquid solution of the biologically active compound at temperatures of 0° to 50°C, preferably 0° to 25°C, under such conditions that there occurs an intimate contact between the two and thus the production of a bond therebetween (the first phase). Ordinarily the biologically active compound will first be placed in a buffer solution, 1 to 10 parts compounds to 1 to 100 parts buffer solution; thereby creating a buffered solution of pH 2 to 11, preferably 3 to 10. The two buffered solutions are then allowed to contact and thereafter the sorption complex is formed. Suitable buffer materials include HCl and other mineral acids as well as solutions of electrolytes and organic water-miscible solvents. The contact times between the buffered solutions, each containing its operative agent will ordinarily be for ½ an hour to 100 hours, preferably 1 hour to 8 hours, though the contact time is not critical.

The thus sorbed biologically active material may be desorbed or dissociated from the hydrogel carrier by a technique know as the second phase. The second phase or desorption is carried out by bringing about a change in the physico-chemical environment of the hydrogel material containing thereon the biologically active material. Broadly speaking the dissociation may be accomplished by varying the pH of the environment, generally downward, such as from 1 to 11, preferably 1 to 10. The pH variance is accomplished by adding such amount parts acid donator to the solution which is necessary to achieve to necessary value pH.

The biologically active compound may also be dissociated by changing the ionic strength of the solvent by adding thereto 1 to 60 parts per 100 weight parts solvent, an electrolyte, or organic water-miscible solvent. The dissociation may also be accomplished by varying the temperature of the environment, such as from 0° to 60°C, preferably 10° to 50°C for a period of time to effect destruction of the sorption complex, ideally that period of time will vary from 2 minutes to 10 hours. Such dissociationing carried out by admixing moving streams of the hydrogel carrier and the solvent solution.

The above described invention can be further defined and illustrated by way of the following Examples which are given by way of illustration only and are not to be interpreted as limiting. All parts, proportions, and ratios therein as wall as in the appended claims, are by weight unless indicated otherwise.

EXAMPLE 1

Isolation of highly active chymotrypsin by affinity chromatography on a hydroxyethyl methacrylate gel with covalently bound tryspin inhibitor was carried out as follows: 0.02 weight parts of crystalline chymotrypsin was dissolved in 1 weight part of 0.05M Tris-HCl buffer solution of pH 8.0. The solution was supplied to a column (10 × 80 mm) containing the hydroxyethyl methacrylate gel, which had been prepared by a suspension copolymerization of 2-hydroxyethyl methacrylate with ethylene dimethacrylate in the presence of an inert solvent, the resulting copolymer had a molecular weight exclusion limit of 300,000. Pancreatic trypsin inhibitor was covalently linked to the gel which was then equilibrated with 0.05M Tris-HCl buffer solution having a pH of 8.0. After the sample had soaked into the column, the column was eluted with the same buffer solution using a flow rate of 300 ml per hour and fractions thereby obtained were collected at ten minute intervals. As soon as the fractions did not contain any compound absorbing in the ultraviolet region of the spectrum (at 280 nm), the elution with 0.05M Tris-HCl buffer solution was stopped and the gel column was further eluted with about 0.1M acetic acid solution having a pH of 3. The dissociation of the sorption complex occurred at the change of pH of the elution agent and chymotrypsin was eluted from the column which exhibited high activity after lyophilization. Its proteolytic activity to hemoglobin and esterase activity to acetylyrosine ethyl ester were measured at a pH of 8; both were related to 1 mg of chymotrypsin. The chymotrypsin concentration was determined photometrically from the absorbance of chymotrypsin solution in 1mM HCl at 280 nm.

EXAMPLE 2

The isolation of a highly active trypsin by affinity chromatography on a hydroxyethyl methacrylate gel with covalently bound trypsin inhibitor was carred out using the same procedure as is described in Example 1, with the exception that the copolymeric gel carrier had a molecular weight exclusion limit of 350,000 and that the esterase activity of the enzymatic preparation refined by the affinity chromatography (trypsin) was determined by means of benzoylarginine ethyl ester.

EXAMPLE 3

This example describes the isolation of antibodies of insulin by means of the antigen (insulin) covalently bound to an ethylene glycol acrylate gel having a molecular weight exclusion limit of 300,000. Antiinsulin serum (2 weight parts) in 0.1M sodium barbiturate buffer having a pH of 8.8 containing 3% of albumin was supplied to the column (8 × 40mm) packed with ethylene glycol acrylate - ethylene diacrylate copolymer, which copolymer contained therein, covalently bound insulin. The gel was equilibrated by washing with 50 weight parts of 0.5M phosphate buffer having a pH of 8.0 containing 0.8M NaCl. After the sample had soaked into the gel, the column was eluted with the same buffer solution. Pure insulin antibodies were eluted from the column using an acid solution (3N HCl) similarly as described in Example 1.

EXAMPLE 4

This example describes the isolation of papain SH-proteinase by affinity chromatography on a hydroxyethyl methacrylate gel (molecular weight exclusion limit of 300,000) with covalently bound p-aminophenyl mercury acetate. The swollen gel above, was activated by cyanogen bromide (50 weight parts) and suspended into 20 weight parts of 10% aqueous dimethylsufoxide. A solution of 1 weight part of p-aminophenyl mercury acetate in 20 weight parts of dimethylsulfoxide was slowly added to the suspension. The suspension was then stirred with a magnetic stirrer at 4°C for 24 hours, heated to 30°C and the gel was decanted 5 times with 150 weight parts of 20% aqueous solution of dimethylsulfoxide. The gel suspension was finally used for packing a column and the gel was eluted with 500 weight parts of 20% aqueous dimethylsulfoxide at a flow rate of 10 ml/hr. The perfectly washed gel obtained in this way was packed into a column 10 × 60 mm and treated with 0.5% solution of papain in a standard buffer (0.5 weight % of butanol, 10 weight % of dimethylsulfoxide, 0.1M KCl, 0.5M sodium acetate, pH 5.0) adapted to 1mM ethylenediamine tetraacetic acid and 10mM $Na_2SO_3$, as long as the absorbance $A_{280}$ of the solution eluted from the column was equal to that of the solution fed into the column. The column was then washed with the standard buffer till the eluate absorbed at a wave length 280nm. The active papain sorbed at the gel was released with the standard buffer solution adapted to 0.5mM $HgCl_2$. A highly active papain was obtained after desalting of the eluate on Sephadex G25 or after dialysis.

EXAMPLE 5

Chymotrypsin inhibitor was isolated from potatoes by means of affinity chromatography on a hydroxyethyl methacrylate gel which gel was crosslinked by ethylene dimethacrylate and carried covalently linked chymotrypsin. Potatoes (1500 weight parts) were homogenized in a high-speed blender and extracted with 200 weight parts of a mixture of 0.9% NaCl and 0.03% $Na_2SO_3$ solutions mixed in a ratio 1:1. The homogenized mixture was kept for 2 hours in a refrigerator at a temperature of +4°C and then was centrifuged. The supernatant was filtered through a 0.5 cm thick layer of kieselguhr and lyophilized. The crude light brown extract was obtained in the yield of 33 weight parts. This crude lyophilized extract (from potatoes 12 weight parts) was dissolved in 75 weight parts of 0.2M Tris-HCl buffer solution of pH 8.0 and after the whole amount had been dissolved the solution was adjusted with 1M NaOH to a pH of 8. The sample was again filtered through the kieselguhr layer and introduced into a column (14 × 455 mm) packed with a hydroxyethyl methacrylate gel carrying covalently linked chymotrypsin and equilibrated with 0.2M Tris-HCl buffer to pH 8. After the sample had soaked into the column, the column was eluted with 0.2M Tris-HCl at pH 8.0 by a flow rate 3.5 ml per hour and fractions were collected each hour. When the fractions indicated that they did not any longer contain any protein, the column was eluted with 0.2M KCl-HCl colution of pH 2.0. By changing pH in the column the inhibitor was eluted in a narrow zone. The inhibition activity of the isolated inhibitor increased 13 times by the single operation.

EXAMPLE 6

The hen ovoinhibitor was isolated from a crude ovomucoid by means of the affinity chromatography on a diethylene glycol acrylate gel with covalently linked trypsin. The crude hen ovomucoid was prepared from white of eggs by means of trichloroacetic acid and acetone (according to Lineweater and Murray [J. Biol. Chem. 171,565 (1947]) and the chymotryptic ovoinhibitor was isolated by the process analogous to that described in Example 5. The inhibition activity of the ovoinhibitor increased 30 times by this single operation.

EXAMPLE 7

The affinity chromatography of a commercial trypsin inhibitor from soybeans was carried out on a column of the hydroxyethyl methacrylate gel having the molecular weight exclusion limit 300,000 carrying covalently linked trypsin by a procedure described in Example 5.

It is thus seen that in the present biologically active compounds are isolated by affinity chromatography. In the system of the invention, a sorption complex is formed between a solvent soluble biologically active compound to be isolated and a biologically active compound chemically linked by a covalent bond to a solid, or hydrogel carrier. The carrier is a hydrophilic macroporous copolymer as heretofore described.

The isolation makes use of the ability of biologically active substances to form specific complexes with other substances, e.g., enzymes form specific complexes with their inhibitors, antibodies with antigens, toxins with antitoxins, receptors with hormones, etc. If one component of the specific complex is bound to a solid carrier, it is possible to adsorb the other component from the solution.

A prime advantage of the separation by affinity chromatography performed in the above described manner is the rapid separation of the isolated biologically active compounds from inhibitors and destructive contaminants.

The sorption complex system has increased porosity, mechanical and hydrolytic properties as compared to systems in which a biologically active compound is linked to a material such as polyacrylamides, glass, agarose or sepharose.

The low degree of porosity of the otherwise essentially desirable solid carriers render them relatively ineffective as adsorbents for purification of enzymes of even low molecular weight. Synthetic polyacrylamide gels also possess many desirable features, but the porosity however, is diminished during the chemical modifications required for attachment of ligands and in this respect the polyacrylamide beads are inferior to those of agarose. While agarose has been recommended, experience with the use of this material explicitly shows that the mechanical and hydrolytical properties are unsatisfactory for the use in technological methods.

The use of carriers on the basis of macroporous methacrylate gels significantly speeds up the process due to the good flow properties of the column and the quick adjustment of the carrier-substrate balance.

1. A method for the isolation of biologically active compounds by affinity chromatography comprising forming a sorption complex between a solvent soluble biologically active compound to be isolated and a biologically active compound linked to a hydrogel carrier by a covalent bond, said hydrogel carrier being a hydrophilic macroporous copolymer formed by copolymerizing at least one hydrophilic monomer selected from the group consisting of:
   A. hydroxyl alkyl acrylates or methacrylates; poly glycol acrylates or methacrylates; amino alkyl acrylates or methacrylates; acrylonitrile or methacrylonitrile;
   acrylic or methacrylic acid of methylolacrylamide copolymerized with another member of said group, or a member selected from the group of cross-linking agents consisting of:

B. glycol polyacrylates or methacrylates; alkylene di acrylates or methyacrylates; alkylene bis acrylamide or methacrylamides; di vinyl benzene; or a member selected from the group consisting of:

C. acrylic and methacrylic acid derivatives, or combinations thereof.

2. A method as defined in claim 1, wherein said biologically active compound is selected from the group consisting of enzymes, enzyme inhibitors, antibodies, antigens and hormones.

3. A method as defined in claim 1, wherein said carriers carrying said biologically active compound is brought into contact with a solvent solution containing a biologically active compound at a pH of 2 to 11 for a period of time sufficient to effect the formation of an adsorption complex therebetween.

4. A method as defined in claim 1, wherein said contact is carried out at temperatures of about −5°C to −50°C.

5. A method as defined in claim 1, wherein said biologically active compound is present in said solvent in amounts of about 0.05 to 30 per 100 parts by weight of said solvent.

6. A method as defined in claim 1, wherein said sorption complex is formed by a period of contact of 30 to 600 minutes.

7. A method as defined in claim 3, wherein said solvent solution is buffered by a member selected from the group consisting of electrolytes and organic water-miscible solvents.

8. A method as defined in claim 3, wherein said sorption complex is formed when equilibrium is reached between said carrier and solvent solution.

9. A method as defined in claim 1, further comprising dissociated said sorption complex and thereafter recovering the other separated biologically active compound.

10. A method as defined in claim 8, wherein said dissociation is carried out by a pH of about 1 to 11.

11. A method as defined in claim 8, whereupon said dissociation is carried out at temperatures of about 0° to 60°C.

12. A method as defined in claim 8, wherein said dissociation is carried out by adding 1 to 60 parts electrolyte per 100 parts solvent to the thus formed adsorption complex.

13. A method as defined in claim 8, wherein said solid carrier is suspended in an inert solvent therefor and thereto there is added a solution of said biologically active compound.

14. A method as defined in claim 1, wherein said carrier is in a form of discrete hydrogel particles.

15. A method as defined in claim 1, wherein said carrier is globular in shape.

16. A method as defined in claim 1, wherein said carrier is in a form of blocks, films, rods, strings, ropes, tapes or belts.

17. A method as defined in claim 8, wherein said dissociation is carried out by passing a solution of said biologically active compound into a vessel containing said carrier.

18. A method as defined in claim 16, wherein said vessel is a column or a reservoir.

19. A method as defined in claim 9, wherein said dissociation is carried out on admixing moving streams of said carrier and said solution.

20. A method as defined in claim 16, wherein a continuous stream of solvent flows countercurrent to said solution of said biologically active compound.

21. A method as defined in claim 1, wherein said carrier is comprised of a copolymer of hydroxy lower alkyl acrylates or methacrylates.

22. A method as defined in claim 1, wherein said carrier is hydroxyethyl methacrylate.

23. The method of claim 1, wherein said copolymer includes a minor amount the cross-linking agent (B).

* * * * *